United States Patent
Ayers

Patent Number: 5,645,569
Date of Patent: Jul. 8, 1997

[54] POST ATRIAL CARDIOVERSION ATRIAL PACING AND METHOD

[75] Inventor: Gregory M. Ayers, Redmond, Wash.

[73] Assignee: InControl, Inc., Redmond, Wash.

[21] Appl. No.: 659,138

[22] Filed: Jun. 4, 1996

[51] Int. Cl.$^6$ ............................................. A61N 1/39
[52] U.S. Cl. ......................................................... 607/4
[58] Field of Search ........................................ 607/4, 5

[56] References Cited

U.S. PATENT DOCUMENTS

| | | | |
|---|---|---|---|
| 5,265,600 | 11/1993 | Adams et al. | 607/4 |
| 5,350,404 | 9/1994 | Adams et al. | 607/5 |
| 5,411,524 | 5/1995 | Rahul | 607/5 |
| 5,514,161 | 5/1996 | Limousin | 607/9 |
| 5,527,345 | 6/1996 | Infinger | 607/4 |

*Primary Examiner*—William E. Kamm
*Assistant Examiner*—George R. Evanisko
*Attorney, Agent, or Firm*—Richard O. Gray, Jr.

[57] ABSTRACT

An implantable atrial defibrillator includes a cardiovertor for applying cardioverting electrical energy to the atria of a heart when the atria are in need of cardioversion. The defibrillator further includes a pacer for pacing the atria of the heart immediately after each application of cardioverting electrical energy to the atria of the heart. The atria are paced in a demand mode and for a finite time period.

22 Claims, 1 Drawing Sheet

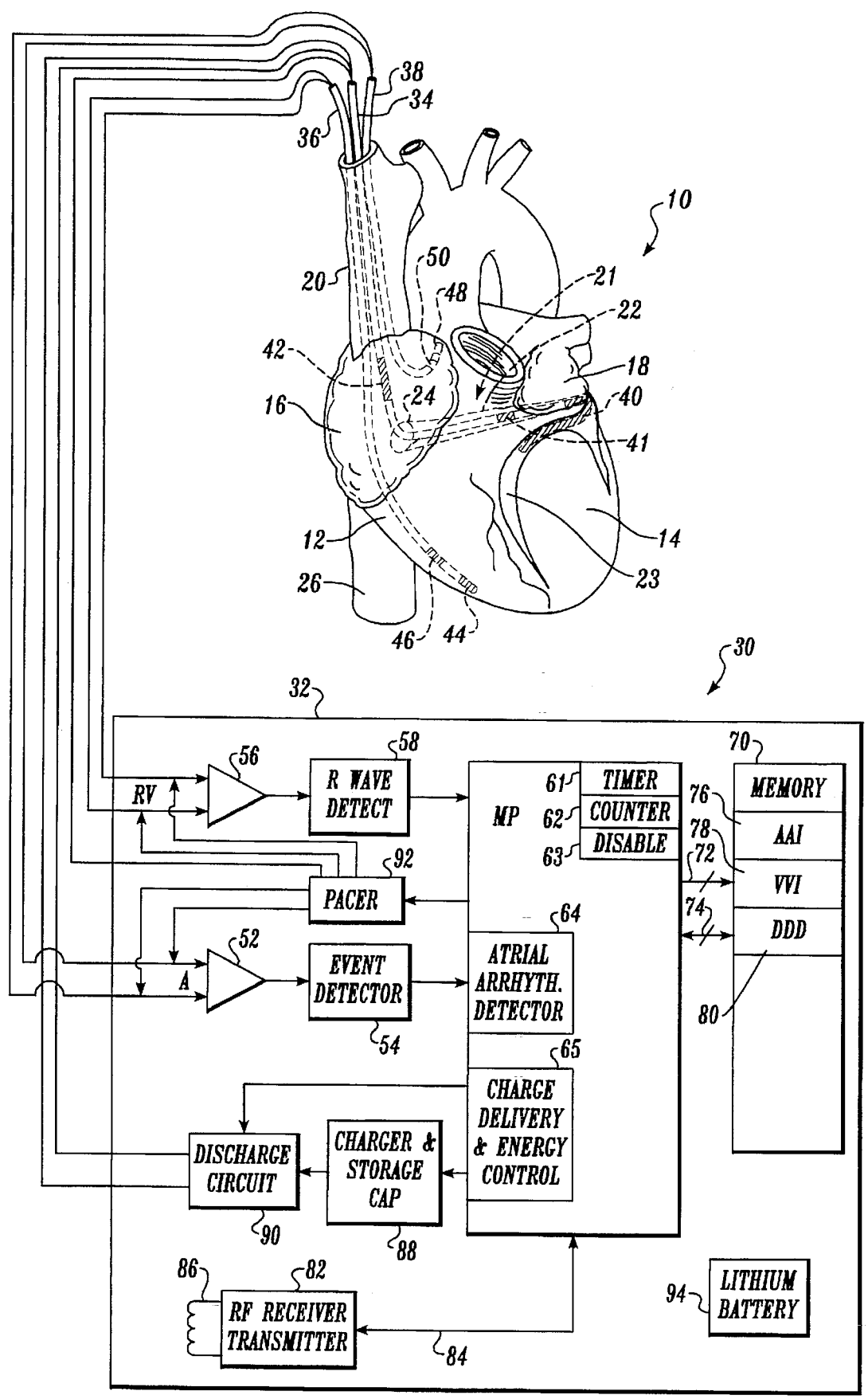

POST ATRIAL CARDIOVERSION ATRIAL PACING AND METHOD

BACKGROUND OF THE INVENTION

The present invention generally relates to an atrial cardiovertor/defibrillator and method for applying cardioverting electrical energy to the atria of a human heart in need of cardioversion. The present invention is more particularly directed to an improved atrial cardiovertor/defibrillator and method wherein after each application of atrial cardioversion therapy, the atria are paced to prevent spontaneous reversion from normal sinus rhythm back to atrial fibrillation.

Atrial fibrillation is probably the most common cardiac arrhythmia. Although it is not usually a life-threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness as a result of reduced cardiac output.

Atrial fibrillation occurs suddenly, and at one time could and in many cases still may only be corrected by an external defibrillator discharging electrical energy to the heart through the skin of the patient. This treatment is commonly referred to as synchronized cardioversion and, as its name implies, involves applying electrical defibrillating energy to the heart in synchronism with a detected R wave of the heart. The treatment is very painful and, unfortunately, most often provides patients only with temporary relief lasting but a few weeks to months.

Drugs are available for reducing the incidence of atrial fibrillation. However, these drugs have many side effects and many patients are resistant to them, which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality. Two such proposed defibrillators, although represented as being implantable, were not fully automatic and required human interaction for cardioverting or defibrillating the heart. Both of these proposed defibrillators required the patient to recognize the symptoms of atrial fibrillation, with one defibrillator requiring a visit to a physician to activate the defibrillator, and the other defibrillator requiring the patient to activate the defibrillator with an external magnet.

An improved atrial defibrillator and lead system which is fully automatic in operation is described in U.S. Pat. No. 5,282,837, which issued on Feb. 1, 1994, for ATRIAL DEFIBRILLATOR AND METHOD, which patent is assigned to the assignee of the present invention and incorporated herein by reference. The defibrillator described in the aforementioned referenced patent automatically detects the presence of an atrial fibrillation episode and applies cardioverting electrical energy to the atria in timed relation to a sensed R wave of the heart. Ventricular pacing is also provided by the described defibrillator.

As can be noted from the above, atrial defibrillators are known that detect for the presence of atrial fibrillation and, if atrial fibrillation is detected, apply therapy to cardiovert the atria. Such therapy may include a single defibrillation electrical shock to the atria utilizing a monophasic, a biphasic, or other waveform shape.

It has been observed however that, in some cases, when normal atrial activity is restored, it may be restored for only a short time, one minute or less, for example, at which time the heart spontaneously reverts from normal sinus rhythm (NSR) back to atrial fibrillation. There are at least three mechanisms that may explain such an occurrence.

The first is that after a cardioverting shock, there may be localized foci of atrial tissue which activate at different times thereby eliminating the possibility of a well organized activation wavefront. The second is that after a cardioverting shock, the heart may experience a bradycardia episode and have no intrinsic rhythm. Absent such intrinsic rhythm, normal areas of the atria may activate on their own, in a disorganized manner resulting in the reinitiation of atrial fibrillation. Lastly, after a cardioverting shock, the atria may experience dispersion of refractoriness so that not all of the atrial cells will be repolarized at any one time. This would render the atria more susceptible to a premature excitation which could in turn cause reinduction of atrial fibrillation. Each of the above mechanisms provides an explanation as to how reinduction of atrial fibrillation could occur.

The present invention provides a solution to the problem of reinitiated of atrial fibrillation regardless of its cause. More particularly, the present invention contemplates pacing the atria after each application of a therapy shock to force all of the atrial tissue to activate and recover together, thereby eliminating the likelihood of a premature or disorganized ectopic beat.

Post-cardioversion pacing is described in copending application Ser. No. 08/243,858, filed May 17, 1994 for IMPLANTABLE ATRIAL DEFIBRILLATOR HAVING AN INTERMITTENTLY ACTIVATED PACING MODALITY. However, the post-cardioversion pacing contemplated therein is to sustain a normal cardiac rate at a time when the normal conduction system of the heart is stunned immediately after an attempted cardioversion. Such pacing is referred to as bradycardia pacing and is performed at a relatively slow rate not necessarily intended to prevent the reinitiation of atrial fibrillation.

SUMMARY OF THE INVENTION

The invention provides a method of cardioverting atria of a heart including the steps of applying cardioverting electrical energy to atria of a heart when the atria are in need of cardioversion and pacing the atria of the heart immediately after applying the cardioverting electrical energy to the atria of the heart.

The invention also provides an implantable atrial defibrillator including cardioverting means for applying cardioverting electrical energy to atria of a heart when the atria are in need of cardioversion and pacing means for pacing the atria of the heart immediately after application of cardioverting electrical energy to the atria of the heart.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the sole figure of which like reference numerals identify identical elements and wherein the sole figure is a schematic block diagram of a fully implantable atrial cardiovertor/defibrillator embodying the present invention, shown in association with a human heart in need of atrial arrhythmia monitoring and potential cardioversion.

DETAILED DESCRIPTION OF THE PREFERRED EMBODIMENT

Referring now to the sole figure, it illustrates a fully implantable atrial cardiovertor/defibrillator 30 embodying the present invention shown in association with a schematically illustrated human heart 10 in need of atrial arrhythmia monitoring and potential cardioversion. The portions of the heart 10 illustrated in the figure are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, and the inferior vena cava 26.

The atrial cardiovertor/defibrillator 30 generally includes an enclosure 32 for hermetically sealing the internal circuit elements of the atrial cardiovertor/defibrillator, to be described hereinafter, an intravascular lead 34, a first endocardial lead 36, and a second endocardial lead 38. The enclosure 32 and the leads 34, 36 and 38 are arranged to be implanted beneath the skin of a patient so as to render the atrial cardiovertor/defibrillator 30 fully implantable.

The intravascular lead 34 generally includes a first or tip elongated electrode 40, a second or ring electrode 41, and a third or proximal elongated electrode 42. As illustrated, the lead 34 is flexible and arranged to be passed down the superior vena cava 20, into the right atrium 16, into the coronary sinus ostium 24, and advanced into the coronary sinus channel 21 of the heart near the left side thereof, so that the electrode 40 is within the coronary sinus channel 21 either within the coronary sinus 22 adjacent the left ventricle 14 and beneath the left atrium 18, or most preferably within the great cardiac vein 23 beneath the left atrium 18. The electrodes 40, 41, and 42 are spaced apart such that when the first electrode 40 is positioned as described above, the third electrode 42 is in the right atrium 16 and the electrode 41 is immediately adjacent the left atrium 18 as shown. The first electrode 40 together with the third electrode 42 provide for the delivery of cardioverting/defibrillating electrical energy to the atria. The second electrode is utilized for pacing the atria in a manner to be described subsequently.

The first endocardial lead 36 preferably includes a bi-polar pair of electrodes 44 and 46, arranged for establishing electrical contact with the right ventricle 12 of the heart 10. The electrodes 44 and 46 permit bi-polar sensing of ventricular activations (R waves) in the right ventricle and pacing of the ventricles. As illustrated, the lead 36 is fed through the superior vena cava 20, into the right atrium 16, and then into the right ventricle 22.

The second endocardial lead 38 also preferably includes a bi-polar pair of electrodes 48 and 50, arranged for establishing electrical contact with the right atrium 16 of the heart 10. The electrodes 48 and 50 are closely spaced apart for sensing localized activity of the right atrium and for pacing the atria. As illustrated, the lead 38 is fed through the superior vena cava 20, into the right atrium 16. The distal end of the lead 38 is substantially "J" shaped in a manner known in the art to position electrodes 48 and 50 in the appendage of the right atrium.

Within the enclosure 32, the atrial cardiovertor/defibrillator 30 includes a first sense amplifier 52, an atrial event detector 54, a second sense amplifier 56, and an R wave detector 58. The first sense amplifier 52 forms a first sensing means which, together with the electrodes 48 and 50 of the second endocardial lead 38 to which sense amplifier 52 is coupled, senses localized activity of the right atrium 16 to provide an electrogram signal to the atrial event detector 54. The second sense amplifier 56 forms a second sensing means which, together with electrodes 44 and 46 of the first endocardial lead 36 to which it is coupled, senses cardiac activity in the right ventricle of the heart to provide a second electrogram signal to the R wave detector 58.

The R wave detector 58 preferably includes a differentiating filter for differentiating the electrogram signal provided by sense amplifier 56. The R wave detector 58 further preferably includes a threshold circuit for setting an upper and lower threshold to provide an output when the upper or lower threshold is exceeded. The thresholds are set, as known in the art, so that only R waves will have sufficient amplitude to exceed the thresholds of the R wave detector.

The atrial event detector 54 similarly preferably includes a differentiating filter for differentiating the first electrogram signal, and a threshold circuit for setting an upper and lower threshold. When the differentiated first electrogram signal transitions beyond either the upper or lower threshold, the atrial event detector 54 provides an output indicating the occurrence of an atrial event.

The enclosure 32 of the atrial cardiovertor/defibrillator 30 further includes a microprocessor 60. The microprocessor 60 is preferably implemented in accordance with this embodiment of the present invention to result in a plurality of functional stages. The stages include a timer 61, a counter 62, and a disable 63. The stages further include an atrial arrhythmia detector 64 and a charge delivery and energy control stage 65.

The microprocessor 60 is arranged to operate in conjunction with a memory 70 which is coupled to the microprocessor 60 by a multiple-bit address bus 72, and a bi-directional multiple-bit data bus 74. This permits the microprocessor 60 to address desired memory locations within the memory for executing write or read operations. During a write operation, the microprocessor stores data in the memory at the addresses defined on the address bus 72, and conveys the data to the memory 70 over the multiple-bit data bus 74. During a read operation, the microprocessor 60 obtains data or mode defining operating instructions from the memory at the storage locations defined on the address bus 72 and receives the operating instructions and data from the memory over the bi-directional data bus 74. To that end, the memory 70 contains memory portions 76, 78 and 80 which contain operating instructions defining single chamber atrial pacing (AAI), single chamber ventricular pacing (VVI) and dual chamber pacing (DDD).

The implantable device 30 is arranged to receive mode selection and other programmable operating parameters from an external controller (not shown) which is external to the skin of the patient. To that end, the enclosure 32 includes a receiver/transmitter 82 for communicating with the external controller. The receiver/transmitter 82 is coupled to the microprocessor 60 over a bi-directional bus 84. The receiver/transmitter 82 receives the programmable operating parameters from the external controller and then conveys the same to the microprocessor 60 for storage in memory 70 or internal cache (not shown). The receiver/transmitter 82 also conveys various information which it obtains from the microprocessor over bus 84 to the external controller.

The receiver/transmitter 82 includes a transmitting coil 86 so that the receiver/transmitter 82 and coil 86, together with the external controller, form a communication system. Such communication systems are well known in the art. One preferred communication system is disclosed in U.S. Pat. No. 5,342,408, which issued on Aug. 30, 1994, for "TELEMETRY SYSTEM FOR AN IMPLANTABLE CARDIAC DEVICE", which patent is assigned to the assignee of the present invention and incorporated herein by reference.

To complete the identification of the various structural elements within the enclosure 32, the atrial cardiovertor/defibrillator 30 further includes a charger and storage capacitor circuit 88 of the type well known in the art which charges a storage capacitor to a selected peak voltage, and a discharge circuit 90 for discharging the storage capacitor within circuit 88 for a predetermined time to provide a controlled discharge output of electrical energy to the atria of the heart when required. To that end, the discharge circuit 90 is coupled to electrodes 40 and 42 of the intravascular lead 34 for applying the cardioverting or defibrillating electrical energy to the atria. Lastly, the cardiovertor/defibrillator 30 includes a pacer 92 and a depletable power source 94. The power source 94 is preferably a lithium battery or other type of battery suitable for providing power to an implantable device such as the atrial cardiovertor/defibrillator 30.

The pacer 92 is coupled to the electrodes 48 and 50 to provide single site pacing of the atria. One output of the pacer 92 is also coupled to electrode 41 for providing, in the alternative, dual site pacing of the atria in combination with either electrode 48 or electrode 50. Lastly, the pacer is coupled to electrodes 44 and 46 for providing pacing of the ventricles. The atrial pacing may be in an atrial demand mode (AAI) and the ventricular pacing may be in a demand mode (VVI) when such pacing is desired. Lastly, the atrial pacing and ventricular pacing may be combined to provide dual chamber demand pacing (DDD).

The pacer 92 may be provided with its own sensing circuitry for detecting atrial and/or ventricular heart activity to support the demand modality function. Alternatively, the pacer may utilize the sense amplifiers 52 and 56 and detectors 54 and 58 for that purpose.

Hence, the pacer 92 may be a stand alone unit within the enclosure 32 and be set into the AAI, VVI, or DDD mode by the external controller communicating with the receiver/transmitter 82. The microprocessor 60 may decode a mode command to cause the pacer 92 to be set in the proper mode and to select either single site or dual site atrial pacing.

Alternatively, and as illustrated in the sole figure, the pacer 92 may be integrated with the microprocessor 60 so that the pacer 92 includes only output circuitry and the microprocessor 60 under control of the operating instructions in memory portions 76, 78 and 80 provides the demand function and the enabling and disabling of the pacer 92. In this case, the sense amplifiers 52 and 56 and detectors 54 and 58 would be utilized for detecting atrial and/or ventricular activity. The disable 63 together with timer 61 disables the post cardioversion pacing after a predetermined pacing period has completed. Alternatively the disable 63 together with the counter 62 may disable the post cardioversion pacing when a preselected number of intrinsic beats have occurred to inhibit pacing.

At spaced apart times, as for example every 5 to 20 minutes, the microprocessor 60 enables sense amplifiers 52 and 56 and detectors 54 and 58 to acquire data representative of the activity of the heart which is stored in the memory 70. The atrial fibrillation detector 64 then processes the stored data to determine if the heart is experiencing an episode of atrial fibrillation. If atrial fibrillation is detected, the charge delivery and control stage 65 initiates the storage of the cardioverting electrical energy within the storage capacitor of charger and storage capacitor circuit 88. When the storage capacitor is fully charged, the microprocessor then preferably initiates a safety protocol as fully described in U.S. Pat. No. 5,207,291 which issued on May 4, 1993 for Atrial Defibrillator and Method For Providing Interval Timing Prior to Cardioversion, which patent is assigned to the assignee of the present invention and incorporated herein by reference. As described in that patent, the microprocessor 60 times the time between successively detected R waves to time the cardiac intervals of the heart. When a cardiac interval is timed which exceeds a predetermined minimum time interval, the microprocessor 60, through the discharge circuit 90, discharges the storage capacitor of circuit 88 for a predetermined discharge time to apply cardioverting electrical energy to electrodes 40 and 42 of lead 34. This applies the cardioverting electrical energy to the atria 16 and 18 of the heart for cardioverting the atria.

After applying the cardioverting electrical energy to the atria, the microprocessor 60, through the disable stage 63, enables the pacer 92 which has been preprogrammed into an AAI or DDD modality. Also, either single site or dual site atrial pacing will have been preselected. This begins the post-cardioversion atrial pacing of the heart. The pacing of the heart continues, preferably at a rate greater than a bradycardia pacing rate, for a finite time until the occurrence of a predetermined event.

In accordance with a first embodiment of the present invention, the predetermined event may be the completion of a timing interval. To that end, the timer 61 may be utilized for timing a time interval beginning immediately after each cardioversion attempt and extending for a time of, for example, 15 seconds to five minutes, and preferably one minute. When the timer 61 completes the timing of the predetermined time interval, the disable stage 63 then disables the pacer 92, the sense amplifiers 52 and 56, and the detectors 54 and 58.

Alternatively, and in accordance with a second embodiment of the present invention, the predetermined event may be the completion of a predetermined number of cardiac cycles. To that end, the counter 62 counts the intrinsic or natural beats of the heart causing the pacer 92 to be inhibited. When the counter 62 has counted a predetermined consecutive number of such beats, for example thirty beats, the disable stage 63 then disables the pacer 92, the sense amplifiers 52 and 56, and the detectors 54 and 58 as previously described.

The atrial defibrillator of the present invention provides atrial demand pacing either in an AAI or DDD mode during only a finite time period following each attempted cardioversion. Hence, the present invention provides an atrial defibrillator having atrial demand pacing during the time when organization of atrial activations is of great importance to prevent a reversion back to atrial fibrillation.

While a particular embodiment of the present invention has been shown and described, modifications may be made. For example other modes of atrial pacing, such as AAO, or other modes of dual chamber pacing, such as DDDR, may be employed for pacing the atria for a finite time following each attempted cardioversion of the atria without departing from the present invention. It is therefore intended to cover in the appended claims all such changes and modifications which fall within the spirit and scope of the invention.

What is claimed is:

1. An implantable atrial defibrillator comprising:
   cardioverting means for applying cardioverting electrical energy to atria of a heart when the atria are in need of cardioversion; and
   pacing means for pacing the atria of the heart responsive to and immediately after each application of cardioverting electrical energy to the atria of the heart by the cardioverting means.

2. An atrial defibrillator as defined in claim 1 wherein the pacing means includes means for pacing the atria in a demand mode.

3. An atrial defibrillator as defined in claim 1 further including disable means for disabling the pacing means in response to an occurrence of a predetermined event.

4. An atrial defibrillator as defined in claim 3 wherein the disable means includes a timer for disabling the pacing means in response to the timer timing a predetermined pacing time period.

5. An atrial defibrillator as defined in claim 1 wherein the pacing means includes means for applying pacing electrical energy to only the right atrium of the heart.

6. An atrial defibrillator as defined in claim 1 wherein the pacing means includes means for applying pacing electrical energy between the right atrium and the left atrium.

7. An atrial defibrillator as defined in claim 1 wherein the pacing means further includes ventricular pacing means for pacing ventricles of the heart in concert with the pacing of the atria.

8. An atrial defibrillator as defined in claim 7 wherein the pacing means includes means for pacing the heart in a DDD mode.

9. An atrial defibrillator as defined in claim 8 further including disable means for disabling the pacing means in response to an occurrence of a predetermined event.

10. An atrial defibrillator as defined in claim 9 wherein the disable means includes a timer for disabling the pacing means in response to the timer timing a predetermined pacing time period.

11. A method of cardioverting atria of a heart, said method including the steps of:

applying cardioverting electrical energy to atria of a heart when the atria are in need of cardioversion; and pacing the atria of the heart responsive to and immediately after applying the cardioverting electrical energy to the atria of the heart.

12. A method as defined in claim 11 wherein the pacing step includes pacing the atria in a demand mode.

13. A method as defined in claim 11 further including the step of terminating the pacing of the atria in response to an occurrence of a predetermined event.

14. A method as defined in claim 13 wherein the terminating step includes timing a predetermined pacing time period and disabling the pacing when the predetermined pacing time period is timed.

15. A method as defined in claim 11 wherein the pacing step includes applying pacing electrical energy to only the right atrium of the heart.

16. A method as defined in claim 11 wherein the pacing step includes applying pacing electrical energy between the right atrium and the left atrium.

17. A method as defined in claim 11 wherein the pacing step further includes pacing ventricles of the heart in concert with the pacing of the atria.

18. A method as defined in claim 17 wherein the pacing step includes pacing the heart in a DDD mode.

19. A method as defined in claim 18 further including the step of terminating the pacing of the atria in response to an occurrence of a predetermined event.

20. A method as defined in claim 19 wherein the terminating step includes timing a predetermined pacing time period and disabling the pacing when the predetermined pacing time period is timed.

21. A method as defined in claim 11 wherein the pacing step includes pacing the atria at a rate greater than a bradycardia rate.

22. An implantable atrial defibrillator comprising:

cardioverting means for applying cardioverting electrical energy to atria of a heart when the atria are in need of cardioversion; and pacing means for pacing the atria of the heart responsive to and immediately after each application of cardioverting electrical energy to the atria of the heart by the cardioverting mean and at a rate greater than a bradycardia rate.

* * * * *